United States Patent [19]

Hase et al.

[11] Patent Number: 4,595,782

[45] Date of Patent: Jun. 17, 1986

[54] PROCESS FOR THE PREPARATION OF ALKALI METAL SALTS OF ACYL CYANAMIDES

[75] Inventors: Christian Hase, Erkrath; Horst Baumann, Leichlingen; Franz-Josef Carduck, Haan; Hubert Pawelczyk, Düsseldorf, all of Fed. Rep. of Germany

[73] Assignee: Henkel Kommanditgesellschaft auf Aktien, Düsseldorf-Holthausen, Fed. Rep. of Germany

[21] Appl. No.: 671,179

[22] Filed: Nov. 14, 1984

Related U.S. Application Data

[63] Continuation of Ser. No. 402,251, Jul. 27, 1982, abandoned.

[30] Foreign Application Priority Data

Jan. 25, 1982 [DE] Fed. Rep. of Germany ....... 3202213

[51] Int. Cl.$^4$ ........................................... C07C 125/08
[52] U.S. Cl. .................................. 564/106; 564/105; 564/103; 260/404.5
[58] Field of Search ................ 564/103, 105, 106; 260/404.5 CN

[56] References Cited

U.S. PATENT DOCUMENTS

3,291,827 12/1966 Huffman et al. .................... 564/106

FOREIGN PATENT DOCUMENTS

2757586 6/1979 Fed. Rep. of Germany .

OTHER PUBLICATIONS

International Critical Tables, vol. VII (1930) pp. 133 and 138.
O. Popowych et al, Non-Aqueous Solution Chemistry, New York (1981) pp. 423 and 424.
L. Osipon et al, *J. Am. Oil Chem. Soc.*, vol. 34 (1957) p. 185.

*Primary Examiner*—Charles F. Warren
*Assistant Examiner*—R. A. Picard
*Attorney, Agent, or Firm*—Hammond & Littell, Weissenberger & Dippert

[57] ABSTRACT

The present invention is for a process for the preparation of alkali metal salts of acyl cyanamides, especially those of aliphatic carboxylic acids by reacting carboxylic acid esters of lower alcohols with monoalkali metal cyanamides. The reaction results in a process which is simple and efficient and one which can be used in commercial scale batch or continuous operations.

15 Claims, No Drawings

PROCESS FOR THE PREPARATION OF ALKALI METAL SALTS OF ACYL CYANAMIDES

This application is a continuation of co-pending U.S. patent application Ser. No. 402,251, filed July 27, 1982, now abandoned.

BACKGROUND OF THE INVENTION

Acyl cyanamides in the form of their alkali salts have been known for a long time. The sodium salt of acetyl cyanamide was described as early at 1878 (J. prakt. Chemie 17 9-11, 1878). The sodium salts of acyl cyanamides of long-chain fatty acids, resin acids or naphthenic acids and their application as soap-like tensides for detergents and wetting agents are known from the British patent specification No. 428,091 of the year 1935 and also from the German patent specification No. 708,428 published in the year 1941. For the preparation of the short- as well as long-chain acyl cyanamides, the respective acid chlorides or acid anhydrides were first reacted with an excess of cyanamide to form the acyl cyanamide, which was then converted to the alkali metal salt in an additional step. A process for the preparation of bifunctional acyl cyanamides, for example adipic acid dicyanamide, by conversion of dicarboxylic acid chloride or dicarboxylic acid ester with cyanamide in alcoholic solution in the presence of substances which have an alkaline reaction and by refluxing is known from the German Offenlegungsschrifts Nos. 20 22 491 and 20 22 492. Similarly, a process for the preparation of sodium formyl cyanamide by conversion of ethyl formate with sodium cyanamide in alcoholic solution by refluxing is described in the German Offenlegungsschrift No. 27 57 586. Finally, substituted cyanoamines, which also include acyl cyanamides of $C_1$-$C_{20}$-carboxylic acids in their general formula, are said to be obtainable by conversion of the amines or amides with cyanogen bromide in benzene according to the European Offenlegungsschrift No. 8 475; the corresponding sodium salt is said to be obtained by dissolving in concentrated sodium hydroxide solution, reaction with ammonium carbonate and extraction with isopropyl alcohol.

Although the acyl cyanamides of the long-chain fatty acids thus are soap-like tensides that have been known for almost 50 years, this type of compound has so far not been given any commercial attention as raw material for detergents. Not the least reason for this are the manufacturing conditions according to the known methods, which are unsuitable for large-scale production. These methods were difficult and time-consuming in the case of the fatty acid chlorides or fatty acid anhydrides as starting materials since the free acyl cyanamides are obtained initially and the preparation of the alkali metal salts requires an additional step.

OBJECTS OF THE INVENTION

It is an object of the present invention to provide an improved process for the production of acyl cyanamides.

It is another object of the present invention to provide a process for the production of acyl cyanamides derived from aliphatic carboxylic acids of 6 to 30 carbon atoms.

Another object of the present invention is to provide a simple and efficient method for the preparation of alkali metal salts of acyl cyanamides which is suitable for commercial scale batch or continuous operations.

A further object of the present invention to react a monoalkali metal salt of cyanamide with a carboxylic acid ester of a lower alcohol at normal pressure and temperatures between 100° to 300° C.

These and other objects of the present invention will become more apparent as the description thereof proceeds.

DESCRIPTION OF THE INVENTION

Now it was found that alkali metal salts of acyl cyanamides, particularly the acyl cyanamides of aliphatic carboxylic acids, can be prepared by reacting the respective carboxylic acid esters with monoalkali metal cycanamide by a process that also can be used with advantage on a commercial scale. The new manufacturing process is characterized by the fact that the carboxylate of a lower alcohol is mixed in eqimolar quantities with a solid, preferably anhydrous monoalkai metal salt of cyanamide and that this mixture is heated to a temperature between 100° and 300° C.

In principle, the process according to the invention does not require any solvent; and it was surprising to find that the reaction between ester and the alkali metal salt of the cyanamide takes place also without the presence of an alcoholic solvent. However, the process according to the invention requires higher initial temperatures than the reflux temperatures of the lower alcohols, i.e., temperatures above 100° C. The lower by product alcohol set free during the formation of the acyl cyanamide collects in the reaction medium and can be removed from it under the proper pressure, by distillation. The esters of the lower alcohols methanol, ethanol or isopropanol are used preferably and the reaction is allowed to take place under normal pressure so that the alcohol is distilled off as it forms, and the amount of alcohol distilled off provides a measure for the continuation of the reaction. The reaction is completed when the alcohol ceases to form and distill off. In the process according to the invention, the formed, low-boiling alcohol may remain if the reaction is performed in a pressure vessel. However, the advantage of the easier agitation of the reaction mixture obtained in this case is more than offset by the disadvantage of having to work in a pressure vessel, which is a complex apparatus. On the other hand, if the ester of an alcohol boiling above the selected reaction temperature at normal pressure is used with the process according to the invention, the conversion can be carried out under reduced pressure, at which the formed alcohol distills over.

For the sake of technological simplicity, the process according to the invention is carried out preferably at normal pressure and without the addition of a low-boiling alcohol as solvent. Under these conditions, the products of the process are obtained in solid form immediately after cooling, and the conversion of the product, which initially collects at the warm temperature as a viscous melt, into prills, needles, flakes, powder or other solid forms suitable for further processing is possible without difficulty. In contrast to the known processes considerably higher reaction temperature at which the forming alcohol distills over continually shortens the reaction time markedly. When the process permits it the operation without solvents may be performed, according to the invention, continuously.

Among acyl cyanamides will be generally understood the carboxylic acid cyanamides themselves and those containing optional groups in the acyl radical. Therefore there can be prepared in accordance with the present invention acyl cyanamides from aliphatic, aromatic, alkyl aromatic and heterocyclic carboxylic acids. The acyl radicals can be substituted as needed, or they may contain heteroatomic bridge members such as an oxy or imino group, for example. The structure of the possible acyl radicals is limited only by the obvious requirement that the acyl radicals or their substutients and bridge members are inert under the reaction conditions. The term acyl cyanamides also includes the derivatives or di- or tricarboxylic acids or generally of polycarboxylic acids.

The process according to the invention concerns above all, the preparation of the alkali metal salts of acyl cyanamides of aliphatic carboxylic acids, preferably of monocarboxylic acids and here particularly the preparation of the alkali metal salts of acyl cyanamides of long-chain aliphatic carboxylic acids with 6 to 30 carbon atoms in the acyl radical. The preparation of the alkali metal salts of acyl cyanamides of the $C_6$–$C_{30}$-fatty acids, especially of the $C_{10}$–$C_{24}$-fatty acids, is a very particular objective of the invention. Of these, the fatty acid cyanamide alkali metal salts of the $C_{12}$–$C_{18}$-fatty acids are most suitable as tensides for use in washing and cleaning agents. Fatty acid cyanamide alkali metal salts can now be prepared in very pure form and in large amounts by the process according to the invention. The invention made the alkali metal salts of the fatty acid cyanamides available as commercially important tenside raw materials on basis of fatty products. These have, in contrast to conventional soaps, lower susceptibility to hydrolysis. The alkali metal salts of the fatty acid cyanamides prepared according to the invention are therefore interesting intermediates for the formulation of new washing and cleaning agents.

The carboxylic acid ester of a lower alcohol used as starting material is particularly the ester of a monovalent lower alkanol with 1 to 5 C-atoms; i.e., the methyl, ethyl, and propyl esters, also the butyl and pentyl esters are used as starting materials. But in principle, the carboxylic acid esters of lower di- and trihydric alcohols can also be used. Under certain conditions, the carboxylic acid ester of glycerin, also particularly the natural fats occurring in the form of triglycerides, are suitable as starting material. The fatty acid triglycerides can be used as carboxylic acid esters when the glycerin formed during the process does not interfere as a contaminent component of the desired product of the process in the subsequent commercial use of the latter, or when its presence is desirable. Consequently, the use of the fatty acid triglycerides as starting materials does not necessitate reaction conditions under which the formed glycerin is distilled off, although the removal by distillation through the choice of reaction temperatures and pressure ranges is basically possible.

But the choice of carboxylic acid ester is generally determined by criteria such as ready commercial availability of the ester and simple performance of the process. Thus the fatty acid methyl esters are the carboxylic acid esters of choice for commercial batch processes.

The solid cyanamide is used in the form of the monoalkali metal salt of lithium, sodium or potassium as the second reaction component in the process according to the invention. The monosodium salt of cyanamide is used preferably mainly for its price. In the process, the dry, i.e. anhydrous, alkali metal salt of cyanmide is given preference when the absence of conventional soap as by-product is important. But the presence of the usual alkali metal soaps as by-products can be in many cases tolerable or even desirable for the subsequent further processing of the product of the process.

The process according to the invention allows a variation of the reaction temperature within broad limits. The lower limit for the reaction temperature range essentially depends on the level of the initial temperature at which the two thoroughly mixed reaction components begin to react with each other, while the upper limit of the reaction temperature is practically determined by the consideration and avoidance of undesirable side reactions, especially discolorations. A reaction temperature in the range from 100° to 250° C. proved to be suitable and preferable for commercial operations. When reaction temperatures in the range of 250° C. or higher are chosen for the process, the problem of thermal decomposition can be avoided by staying within the process time, which is short under these conditions.

The progress of the process can generally be measured by the alcohol formation; or by determining the amount of remaining ester e.g. by gas chromatography or as the portion insoluble in water. Infrared spectroscopy is well-suited for the determination of the reactants since all reactants have characteristic, strong absorption at different wave lengths, e.g.:

NaHNCN: 2120 and 2170 cm$^{-1}$;
fatty acid esters: about 1750 cm$^{-1}$;
stearic acid cyanamide-Li: 2180, 1600 and 1390 cm$^{-1}$;
stearic acid cyanamide-Na: 2160, 1515 and 1390 cm$^{-1}$;
stearic acid cyanamide-K: 2160, 1560 and 1380 cm$^{-1}$.

The alkali metal salts of the fatty acid cyanamides are solid, colorless to slightly yellowish substances with a brittle to waxy consistency at room temperature. They soften at higher temperatures and melt above 100° to 150° C., depending on their composition, to form viscous liquids. The melting points are not characteristic. The technically especially interesting fatty acid esters of naturally occurring fatty acids are generally used as mixtures, i.e. as compounds with fatty acid radicals of varying lengths, and a sharp melting point consequently cannot be expected as a characteristic of the substance.

The choice of equipment in which the process according to the invention can be carried out depends on the batch sizes and the rheological properties of the reaction mixture at the chosen reaction temperature. Acceptable are, e.g., conventional heated agitator tanks, kneading machines, but also tube reactors with attachments for the recovery of the free alcohol. After the reaction is completed, the products of the process can be conveyed directly as melts, e.g. through heated pipes, for further processing. According to another processing variation, the melts can be turned into a solid form suitable for storage or further processing by converting them into prills, needles or flakes. The preparation of an aqueous concentrate by dissolving in water is also possible, but the very fact that the alkali metal salts of the fatty acid cyanamides can be obtained directly in dry form is an advantage for many applications. It is well known that the most important commercial tensides of the sulfonate and sulfate type are used as aqueous paste concentrates for large-scale operations. However, the water content of these pastes frequently is considered a disadvantage, for example in the manufacture of detergent powders by hot spray-drying of an aqueous slurry in spray towers. In this important large-scale process for the preparation of detergents in powder form, it is an advantage when the active substances contain as little water as possible to keep the water content in the slurry. In this case the amounts of energy required for the removal of the water during the subsequent spray-drying is also low.

Another aspect of the invention concerns the supply of the alkali metal salts of the acyl cyanamides in a form that does not have in the melt the generally high viscosity of the pure compounds and which is therefore easier to pump and agitate. This additional example of the invention is characterized by the addition of a high-boiling, water-soluble substance, which is inert under the reaction conditions, as a flux for the reaction components. Suitable as fluxes are mainly substances that do not interfere during the subsequent further processing of the product of the process by their presence; particularly suitable as additives are those substances the presence of which is expressly desired during further processing of the product. In the case of the further application of the products as tensides for the preparation of detergents and cleaning agents, the suitable flux additions are especially polymerization products with ethylene oxide and/or propylene oxide, e.g. polyethylene glycols, block polymers of ethylene oxide and propylene oxide, adducts of ethylene oxide and/or propylene oxide with long-chain alcohols, alkyl phenols or fatty acid amides. The nonionic tensides, which frequently are components of detergent and cleaning agent formulations, also belong to this group of compounds. The addition of a flux usually also results in a lowering of the initial temperature. In the broadest sense, the glycerin forming in situ, after the addition of fatty acid triglycerides as starting material, is also to be considered a flux. In this case, the process conditions with respect to temperature and pressure are chosen to keep the formed glycerin in the reaction medium. The alkali metal salts of the fatty acids, i.e. the conventional soaps, are also suitable as fluxes. Again, soap does not need to be added separately; rather, it is possible and also advantageous in this case to use an incompletely dried, i.e. still hydrous alkali metal cyanamide as a reactant, so that the soap is formed in situ as flux during the reaction. The essentially identical result can be obtained by the use of anhydrous alkali metal cyanamide together with alkali metal hydroxide.

The following examples are given by way of explanation and not by way of limitation.

EXAMPLES

EXAMPLE 1

In a 1 liter three-neck flask with agitator, internal thermometer and attached distillation bridge, 253 g (1.5 mole) methyl ester of the first cut of coconut fatty acids (saponification number 332) containing mainly $C_6$–$C_{12}$ fatty acids were well agitated with 96 g (1.5 mols) anhydrous monosodium cyanamide, and the mixture was heated to 155° C. Most of the methanol formed distilled over within two hours, while the contents of the flask thickened but remained sufficiently fluid for agitation. The contents of the flask were poured out and congealed into a brittle, whitish solid that formed a clear solution in water. The infrared spectrum of the reaction product had characteristic absorptions at 2160, 1515 and 1390 $cm^{-1}$, which identified the product as the sodium salt of carboxylic acid cyanamide.

EXAMPLE 2

In the equipment described in Example 1, 270.5 g (1 mol) commercial grade isopropyl myristate and 64 g (1 mol) monosodium cyanamide were heated in the same manner to 170° C. for 2½ hours. The isopropyl alcohol formed during the reaction was almost completely distilled off after 2 hours. The reaction product was obtained as highly viscous paste that could not be poured from the flask. The product congealed upon cooling into a brittle, whitish solid that produced a clear solution in water. The yield was quantitative.

EXAMPLE 3

In a 1 liter three-neck flask with agitator and thermometer, 289.2 g (0.33 mol) of a technical grade triglyceride mixture of palmitic and stearic acid (hardened tallow) (saponification number 194) and 64 g (1 mol) monosodium cyanamide were heated to 160° C. The contents of the flask thickened after only 15 minutes, but were easy to agitate. The reaction mixture was poured out after 30 minutes at 160° C. and congealed upon cooling into a wax-like solid that produced a clear solution with water. Yield 345 g (97%). The infrared spectrum of the product showed the bands of glycerin in addition to the characteristic acyl cyanamide bands.

EXAMPLE 4

In a 500 ml three-neck flask with agitator, thermometer and attached distillation bridge, 100 g (0.42 mol) of a methyl ester of coconut fatty acid (saponification number 235) (chain length $C_{12}$–$C_{18}$) and 27 g (0.42 mol) anhydrous monosodium cyanamide were mixed and quickly heated to an internal temperature of 240° C. with an oil bath preheated to 260° C.

The formation of methanol began after 15 minutes and was completed after an additional period of ten minutes. The reaction mixture became viscous during this process. After a total time of 30 minutes, the infrared spectrum of a sample was recorded and the absence of ester absorption bands was established. The viscous product was poured out and congealed into a yellowish solid that dissolved readily in water. The product had the characteristic IR-spectrum of the sodium salts of fatty acid cyanamide. Yield 256 g (95%).

EXAMPLE 5

In the apparatus of Example 4, 143.7 g (0.5 mol) of the methyl ester of the hydrogenated tallow fatty acids acids (saponification number 195) and 40 g (0.5 mol) monopotassium cyanamide were mixed and heated to 160° C.–170° C. for 2 hours. Then, the viscous reaction product was poured out; it congealed upon cooling into a yellowish, water-soluble solid. The product was identified as acyl cyanamide potassioum salt by its infrared spectrum. Yield 154 g (92%).

EXAMPLE 6

In the apparatus described in Example 1, 230.4 g of the methyl ester of coconut fatty acids (saponification number 243.5), 64 g (1 mol) monosodium cyanamide and 50 g of the adduct of 10 mols ethylene oxide and tallow alcohol (trade name Eumulgin 010, registered trademark) were mixed and heated to 160° C. The reaction was complete after 3 hours, when practically the total calculated amount of methanol had distilled over. After a total reaction time of 5 hours, the thin and easily agitated contents of the flask were poured out. After cooling, the reacton product was obtained as a wax-like white-yellowish, readily water-soluble mass. The product showed the typical bands of aliphatic ethers in addition to the characteristic bands of the sodium salt of fatty acid cyanamide. Yield 289 g (93%).

EXAMPLE 7

In a batch that otherwise corresponded to that in Example 1, only 1.3 mols of the monosodium cyanamide instead of 1.5 mols of this salt were used together with 0.2 mol NaOH. The sodium soap formed besides the sodium acyl cyanamide during the reaction. The reaction mixture was easier to agitate and congealed upon pouring into a light-colored, wax-like solid. Its infrared spectrum showed the carbonyl bands of the soap at 1560 cm$^{-1}$ in addition to the bands of acyl cyanamide salt.

EXAMPLE 8

In analogy to Example 2, 298.5 g (1 mol) stearic acid methyl ester each were reacted in three different batches with 1 mol monolithium cyanamide (48 g) or 1 mol monosodium cyanamide (64 g) or 1 mol monopotassium cyanamide (80 g) at 150°–170° C. Reaction time 2–3 hours. The respective products—lithium salt of stearic acid cyanamide, sodium salt of stearic acid cyanamide, potassium salt of stearic acid cyanamide—were each obtained in quantitative yields in the form of slightly yellowish solids.

EXAMPLE 9

This example describes a continuous method of the process according to the invention. A suspension of 6.80 kg (106.3 mols) anhydrous monosodium cyanamide in 25.0 kg (106.3 mols) of a methyl ester of coconut fatty acids ($C_{12}$–$C_{18}$) with the saponification number 238 was heated to 60° C. and was fed continuously into a screw reactor that was heated to 240° C. The feeding rate was 0.6 liter/minute, which resulted in a mean reaction time of approximately 20 minutes for the given effective reactor volume of approximately 11 liters. The methanol, which escaped through the vapor outlets, was condensed in a descending glass cooler, while the formed sodium salt of the fatty acid cyanamide was transferred with the aid of an attached extruder to a flaking drum.

The product congealed on the drum, which was cooled with tap water, and was obtained in the form of weakly-yellow-colored, completely water-soluble flakes. The infrared spectrum of the product showed the bands characteristic for sodium salts of fatty acid cyanamide at 2160, 1515 and 1390 cm$^{-1}$. The yield was 27.9 kg (98%); 3.1 kg methanol (91%) were also collected.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the preparation of alkali metal salts of acyl cyanamides of aliphatic carboxylic acids which comprises reacting equimolar amounts of a lower alcohol ester of a fatty acid having from 6 to 30 carbon atoms with a mono-alkali metal cyanamide by heating a mixture thereof to temperatures between 100° and 300° C., in the absence of added solvent.

2. The process as set forth in claim 1 wherein the mono-alkali metal salt of the cyanamide is anhydrous.

3. A process according to claim 1 wherein the operating temperature chosen is such that the free alcohol resulting from the reaction is distilled off.

4. A process according to claim 1 wherein the reaction is carried out at ambient pressure.

5. A process as set forth in claim 1 wherein the reaction temperature is in the range of from 100° to 250° C.

6. The process as set forth in claim 5 wherein the fatty acid moiety contains 12 to 18 carbon atoms.

7. A process according to claim 6 wherein the $C_{12}$–$C_{18}$-fatty acid ester is a methyl ester.

8. A process according to claim 1 wherein the monoalkali cyanamide is monosodium cyanamide.

9. The process as set forth in claim 8 wherein the monosodium cyanamide is anhydrous.

10. A process as set forth in claim 1 wherein there is added a high-boiling, water-soluble, liquid or pastelike substance which is inert to the reactants as a flux to promote the fusion of the reactants.

11. A process as set forth in claim 10 wherein the flux is a polymerization product with ethylene oxide and/or propylene oxide.

12. A process as set forth in claim 10 or 11 wherein the flux is a nonionic tenside.

13. A process as set forth in claim 1 wherein the carboxylic acid ester is a higher fatty acid triglyceride.

14. A process as set forth in claim 1 wherein the mono-alkali metal cyanamide contains water or is a mixture of anhydrous monoalkali metal cyanamide and alkali metal hydroxide.

15. The process of claim 1, wherein the fatty acid has from 10 to 24 carbon atoms.

* * * * *

UNITED STATES PATENT AND TRADEMARK OFFICE
CERTIFICATE OF CORRECTION

PATENT NO. : 4,595,782
DATED : June 17, 1985
INVENTOR(S) : CHRISTIAN HASE et al.

It is certified that error appears in the above-identified patent and that said Letters Patent is hereby corrected as shown below:

Column 8, Claim 6, line 1, "claim 5" should read -- claim 15 --.

Signed and Sealed this

Twenty-third Day of September 1986

[SEAL]

Attest:

DONALD J. QUIGG

Attesting Officer     Commissioner of Patents and Trademarks